(12) United States Patent
Kaufman et al.

(10) Patent No.: US 7,176,023 B2
(45) Date of Patent: Feb. 13, 2007

(54) ENDOTHELIAL CELLS DERIVED FROM PRIMATE EMBRYONIC STEM CELLS

(75) Inventors: Dan S. Kaufman, Woodbury, MN (US); Rachel Lewis, Madsion, WI (US); Robert Auerbach, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 472 days.

(21) Appl. No.: 10/287,334

(22) Filed: Nov. 1, 2002

(65) Prior Publication Data

US 2003/0166273 A1 Sep. 4, 2003

Related U.S. Application Data

(60) Provisional application No. 60/335,332, filed on Nov. 2, 2001.

(51) Int. Cl.
*C12N 5/00* (2006.01)
(52) U.S. Cl. .................. 435/377; 435/325; 435/366
(58) Field of Classification Search ............... 435/325, 435/366, 377
See application file for complete search history.

(56) References Cited

U.S. PATENT DOCUMENTS

| | | | |
|---|---|---|---|
| 5,691,203 A * | 11/1997 | Katsuen et al. ............. | 435/402 |
| 5,817,773 A | 10/1998 | Wilson et al. | |
| 5,843,780 A | 12/1998 | Thomson | |
| 5,879,383 A * | 3/1999 | Bruchman et al. ......... | 623/2.42 |
| 6,200,806 B1 | 3/2001 | Thomson | |
| 6,632,424 B1 | 10/2003 | Lyman et al. | |

FOREIGN PATENT DOCUMENTS

WO     WO 97/47734     12/1997

OTHER PUBLICATIONS

Rathjen et al. Reprod Fertil. Dev. Oct. 1998 pp. 31-47.*
U.S. Appl. No. 10/128,738, filed Oct. 23, 2003, Itescu.
U.S. Appl. No. 10/211,522, filed Oct. 16, 2003, Istkovitz-Eldor et al.
U.S. Appl. No. 10/348,359, filed Jan. 29, 2004, West.
Balconi, G, et al., "Development of Endothelial Cell Lines From Embryonic Stem Cells," Arterioscler Thromb Vasc Biol., (2000) 20:1443-1451.
Carmeliet, P., "Mechanisms of Angiogenesis and Arteriogenesis," Nature Medicine (2000) 6:389-395.
Choi, K, et al., "A Common Precursor for Hematopoietic and Endothelial Cells," Development (1998) 125:725-732.
Cines, DB, et al., "Endothelial Cells in Physiology and in the Pathophysiology of Vascular Disorders," Blood (1998) 91:3527-3561.
Gehling UM, et al., "In vitro Differentiation of Endothelial Cells from AC133-positive Progenitor Cells," Blood (2000) 95:3106-3112.
Hirashima, M, et al., "Maturation of Embryonic Stem Cells Into Endothelial Cells in an In Vitro Model of Vasculogenesis," Blood (1999) 93:1253-1263.
Jackson, KA, et al., "Regeneration of Ischemic Cardiac Muscle and Vascular Endothelium by Adult Stem Cells," The Journal of Clinical Investigation (2001) 107:1395-1402.
Kalka, C, et al., "Transplantation of ex vivo expanded endothelial progenitor cells for therapeutic neovascularization," PNAS (2000) 97:3422-3427.
Levenberg, S, "Endothelial cells derived from human embryonic stem cells," PNAS (2002) 99:4391-4396.
Yamashita, J, et al., "Flk1-positive cells derived from embryonic stem cells serve as vascular progenitors," Nature (2000) 408:92-96.
Papadimitriou, E., et al., "Endothelial Cell Proliferation Induced by HARP: Implication of N or C Terminal Peptides," Biochem. and Biophys. Res. Comm. 274:242-248 (2000).

* cited by examiner

Primary Examiner—Leon Blaine Lankford, Jr.
(74) Attorney, Agent, or Firm—Quarles & Brady LLP

(57) ABSTRACT

A method is described to induce primate embryonic stem cells to differentiate into a relatively homogenous population of endothelial cells. The ES derived endothelial cells have the general morphological and cell surface marker characteristics of endothelial cells. The ES derived endothelial cells also are capable of inducing and participating in blood vessel formation (or vascularization) when transplanted into tissue in vivo.

4 Claims, No Drawings

ENDOTHELIAL CELLS DERIVED FROM PRIMATE EMBRYONIC STEM CELLS

CROSS-REFERENCE TO RELATED APPLICATIONS

This application claims priority from U.S. Provisional Patent Application No. 60/335,332 filed Nov. 2, 2001.

STATEMENT REGARDING FEDERALLY SPONSORED RESEARCH OR DEVELOPMENT

To be determined.

BACKGROUND OF THE INVENTION

Stem cells are defined to be cells which are capable both of self-renewal and differentiation into one or more differentiated cell types. Human embryonic stem cells are a category of stem cells created from human pre-implantation blastocysts. Human embryonic stem cells are pluripotent and may be totipotent, meaning that they can certainly differentiate into many cell types evidenced in an adult human body and may be capable of differentiating into all cell types present in the human body.

Embryonic stem cells (ES cells) have also been derived in a number of animals other than humans. For example, much scientific work has been conducted with murine ES cells. Once a method for the initiation of ES cell cultures for a particular species is worked out, it becomes possible to manipulate the ES cells, and animals which result therefrom, in a variety of ways to learn useful information about the genetics of the animal under study. For example, it has become possible over the past decade to create cultures of murine ES cells in which one or another specific gene is knocked out in each murine stem cell culture. While some techniques that could be worked out in murine ES cell systems were transferable to other species, many were not. For example, the basic techniques which could be used to create murine ES cell cultures did not transfer well to many other animal species. For the development of techniques for the culture and manipulation of human ES cells, the murine cell may therefore not be the best model due to the phylogenic distance between humans and mice. However, in the course of the development of the science of human ES cell cultures and techniques, much of the preliminary work was conducted in non-human primates, such as the rhesus monkey. Other primate ES cell cultures have proven to be a relatively reliable model for systems that could be easily transferred to human cell culture. For an example, murine ES cell cultures require application of leukemia inhibitory factor (LIF) or another agonist of the gp130/STAT3 signaling pathway for maintenance of undifferentiated cell growth, whereas human and rhesus monkey ES cell cultures do not require LIF for undifferentiated cell growth. Prior work on hematopoiesis using rhesus monkey ES cells validates the utility of this system for doing pre-clinical investigations for techniques that can be transferred to human ES cell cultures.

One of the exciting potential uses of stem cells is for human tissue transplantation. It is hoped and expected that techniques can be developed to direct the differentiation of stem cells into specific lineages which can then be transferred into the human body to replace or enhance tissues of the body. In order to do that, first techniques must be developed to direct the differentiation of stem cells into the specific cell lineages desired. Techniques have already been proposed to direct stem cell cultures into lineages of hematopoeic, neural, cardiomyocyte, pancreatic and other lineages. These techniques have proven to be quite different from each other and independent in the sense that a new and different technique is required for each new desired lineage.

Endothelial cells make up a network of interconnected cells in the human body that line blood vessels, lymphatic vessels, and form capillaries. Endothelial cells regulate the flow of nutrient substances and create and respond to diverse biologically active molecules. While it has been demonstrate that human ES cells will differentiate into many progeny cells types, including endothelial cells, it has not been previously possible to create distinct cultures of derivatives of human ES cells directed into an endothelial lineage.

BRIEF SUMMARY OF THE INVENTION

The present invention is summarized in that a method has been developed which permits the direct differentiation of a culture of embryonic stem cells into a culture of endothelial cells. The method includes culturing the embryonic stem cells in a culture medium previously known to maintain endothelial cells and which, it now turns out, has the capability to support embryonic stem cells in the process of differentiation into endothelial cells.

The present invention is also summarized in that cultures of endothelial cells derived from embryonic stem cells which have morphology and cell surface markers characteristic of endothelial cells and which are capable of inducing vascularization of tissue in vivo.

It is a feature of the present invention in that it is relatively efficient to perform since its steps are simple, and the result is a culture that appears to be a relatively homogenous population of endothelial cells.

Other objects, advantages and features of the present invention will become apparent from the following specification when taken in conjunction with the accompanying drawings.

BRIEF DESCRIPTION OF THE SEVERAL VIEWS OF THE DRAWINGS

Not applicable.

DETAILED DESCRIPTION OF THE INVENTION

The present invention is directed both to a method to direct the differentiation of primate embryonic stem cells into endothelial cells and to the relatively pure population of endothelial cells so produced. The method is based on the cultivation of primate embryonic stem cells with a defined protein growth factor or factors which cause the cells so treated to change their morphology to become endothelial cells. In contrast to other techniques for the directed differentiation of cells of other lineages from embryonic stem cells, the culture of endothelial cells, derived from embryonic stem cells by the method described here, appears relatively uniform and is made up of primarily of endothelial cells having apparent angiogenic capability.

The culture method is based on the culture of undifferentiated primate embryonic stem (ES) cells in a medium containing vascular endothelial cell growth factors (VEGF), basic fibroblast growth factor (bFGF), insulin-like growth factor (IGF-1), and epidermal growth factor (EGF). These factors are all found in a commercially available medium known as endothelial cell basal medium (EBM-2, Clonetics/BioWhittaker). This medium was previously known and is used to sustain endothelial cells in culture. It was not previously known that this medium could be used to support the differentiation of ES cells into endothelial cells. While this combination of growth factors has been found to be sufficient to support the differentiation of ES cells into endothelial cells, it may not be necessary to use all four factors in the culture medium, and whether or not one of the factors can be omitted can readily be ascertained by empirical experimentation without departing from the concept of the present invention.

What separates this method from prior art derivation of heterogeneous mixtures including endothelial cells is the relative uniformity of the transition of the cell culture from ES cells to endothelial cells. Other methods were tried, without success, to achieve this transition, such as application of phorbol esters, co-cultivation with stromal cells plus serum and isolation of endothelial cells from embryoid bodies. None of these efforts reproducibly yielded cultures of predominantly endothelial cells. In contrast, the method described here is simple and efficient and results in a cell culture of morphologically similar cells having the characteristics of endothelial cells.

The culture of endothelial cells made by the present invention will have certain characteristics. The cells have a characteristic morphology, similar to elongated or stellate shaped endothelial cells. In contrast, ES cells grown in other media differentiate into a heterogeneous population of cell types with no distinct endothelial-appearing cells. The endothelial cells rapidly form tubular structures when placed in Matrigel (™) medium. The endothelial cells are positive for presence of the von Willebrand factor (vWF) and have high levels of *Ulex europaeus* agglutinin 1 (UEA-1) binding, as well as expression of the intergrin $\alpha v\beta 3$ and the surface antigen CD146. These cells also will take up acetylated LDL, another trait characteristic of endothelial cells. These cells do lack expression of CD31 and VE-cadherin, two antigens commonly, but not always, present on the surface of endothelial cells. These endothelial cells have the ability, when transferred into a SCID (severe combined immunodeficient) mouse together with tumor cells, to effect the vascularization of the resulting tumor, thus demonstrating the ability of the cells both to recruit and to participate in vascularization in vivo. The ability of these cell to participate in vascularization is particularly noteworthy, since that attribute makes in possible to transplant genetically altered endothelial cells into a tissue requiring vascularization with the altered cells surviving in vivo in the vascular matrix created to therefore express whatever gene was inserted into the cells.

In contrast to other cell types which can be induced to form from embryonic stem cells, the endothelial cell culture described and characterized here is relatively homogenous in cells committed to the derivative lineage, i.e. to be endothelial cells. The ES derived endothelial cell culture is formed of cells having a uniform morphology and exhibiting the characteristics of endothelial cells. Given the limits of present cell culture technology, however, it cannot be said with certainty that the ES derived endothelial cell culture is entirely free of other cell types. What can be said is that the ES derived endothelial cell culture is predominantly composed of endothelial cells and is a practical source of cells which will act as endothelial cells to promote and participate in vascularization of tissues when transplanted into a host in vivo. Using a common test for endothelial character, the ability to bind the *Ulex europaeus* agglutinin 1 (UEA-1) lectin, it has been found that reproducible over 90% of the cells in the derivative culture do bind the UEA-1 lectin.

While in some variations of the method the percentage of cells which bind to UEA-1 might vary, in cultures of endothelial cells made by the method described here, at least 75%, and more preferably, over 90%, of the cells in the culture will test positive for the ability to bind the UEA-1 lectin.

While the examples below were conducted with rhesus monkey ES cells, the same processes and result can be obtained with human ES cells. Human endothelial cells derived from ES cells offer the possibility to develop tissues transplantable into human patients. Transplantation of endothelial cells would be desirable for those applications in which vascularization of ischemic tissue is needed. In addition, the introduction of endothelial cells may be useful in any location on the body where improved vascularization is needed. Since the precursor ES cells can be grown in any number, this makes possible the generation of large numbers of endothelial cells for clinical experimentation or treatment.

EXAMPLES

Methods
Cell Culture

Undifferentiated rhesus monkey ES cells (R366.4 cell line) were cultured as previously described (Thomson et al. Proc. Natl. Acad. Sci. USA 92:7844–7848 (1996)). Briefly R366.4 cells were co-cultured with irradiated mouse embryonic fibroblast (MEF) cells in medium containing DMEM, 20% FBS (Hyclone, Ogden Utah), 2 mM L-glutamine (Sigma, St. Louis, Mo.), 0.1 mM 2-mercaptoethanol (Sigma), and 1% MEM non-essential amino acids (Invitrogen). Undifferentiated cells were fed daily with fresh medium and passaged onto new MEFs approximately every 5–7 days. To promote endothelial cell differentiation, the medium was removed from the ES cells 24 hours after plating and replaced with medium consisting of EGM2, 5% FBS, VEGF, bFGF, IGF-1, EGF, and ascorbic acid (EGM2) (EGM2-MV Bullet Kit, Clonetics/BioWhittaker, Walkersville, Md.). The ES cells were differentiated for 29 days in the EGM2 medium, which was changed every 3–5 days. Differentiated rhesus ES cells, were dissociated with 0.05% trypsin/0.53 mM EDTA (GIBCO/BRL) for 5 minutes, centrifuged, and re-plated in EGM2 in 10 cm tissue culture dishes without irradiated MEF cells. After 24 hours non-adherent cells were removed and adherent cells were fed fresh medium. The rhesus ES cell-derived endothelial cells (RESDECs) could be grown to confluence and serially passaged and expanded in the EBM2 medium.

Human umbilical vein cells (HUVECs) (Clonetics/Biowhittaker) were also grown and passaged in EGM2 by known methods.

Tube Formation on Matrigel 0.2 ml of Matrigel (Becton Dickinson) was added to each well of a 24 well tissue culture plate and allowed to solidify at 37° C. for at least 30 minutes. Following gelation, 0.2 ml of a cell suspension containing $5\times10^4$–$1\times10^5$ RESDECs was placed on top of the Matrigel. The cultures were incubated at 37° C./5% $CO_2$ and observed at 24, 48, and 72 hours for rearrangement of cells into tube-like capillary structures. Individual experiments were performed in triplicate and representative wells recorded by photomicrography.

VEGF and bFGF ELISA

RESDECs were cultured for 3 days in the absence of VEGF or bFGF in EGM2, EGM2 supplemented with 10% Knockout serum replacer (GIBCO) instead of FBS, or DMEM supplemented with 10% FBS. After 72 hours the conditioned media (CM) was collected and centrifuged to remove dead cells. EGM2 medium alone served as a negative control. The amount of VEGF or bFGF in the CM was analyzed by colorimetric ELISA assay (R & D systems, Minneapolis, Minn.).

Flow Cytometry

RESDECs were washed with $Ca^{2+}$ and $Mg^{2+}$ free PBS and detached from the monolayer with 0.05% trypsin/0.53 mM EDTA for 5 minutes. The dissociated cells were centrifuged and washed with FACS medium consisting of PBS supplemented with 2% FBS and 0.1% sodium azide. After filtration through 80-micron nitex, the single-cell suspension was measured in aliquots and stained with either isotype control or antigen-specific antibodies diluted to appropriate concentrations in FACs media. Cell surface antigen expression was analyzed using antigen-specific primary antibody followed by fluorescent-tagged secondary antibodies (indirect staining), or fluorescently-conjugated antigen-specific antibodies (Direct staining). Appropriate unconjugated mouse and goat IgGs (both Sigma) as well as FITC-conjugated mouse IgG (Pharmingen San Diego, Calif.)) were used as isotype controls. Unconjugated antigen-specific antibody against flk-1 (Research Diagnostics) was detected with a FITC labeled anti-goat IgG antibody (Sigma). Unconjugated antibodies against VEGF receptor 1 (Flt-1) and VEGF receptor 2 (flk-1) (both Sigma) were detected with a FITC labeled goat anti-mouse IgG (Caltag). Unconjugated P1H12 antibody (mouse IgG1, provided by Dr. Robert Hebbel, University of Minn.) was detected with rat anti-mouse IgG-FITC conjugated secondary antibody (Caltag). The cells were also tested for expression of the VEGF receptor using a biotinylated VEGF Kit (R&D Systems) and for their ability to bind the *Ulex europaeus* agglutinin 1 (UEA-1) (Vector labs). Direct conjugated antibodies used were HLA-A, B, C-FITC (Pharmingen) and αVβ3/cl LM609-FITC (Chemicon). Human umbilical vein cells (HUVEC) (Clonetics) served as a positive control. Cells were analyzed without fixation on a FACScan or FACs Calibur (Becton Dickinson) using propidium iodide to exclude dead cells. Data analysis was carried out using CellQuest software (Becton Dickinson).

Immunostaining

Analysis for the acetylated LDL receptor was performed by diluting diIAcLDL (Molecular Probes) in serum-free EGM2. Cells were washed twice and incubated overnight in EGM2 medium containing diIAcLDL. After washing, the cells were observed by fluorescence microscopy (UV, rhodamine filter). HUVECs were used as a positive control.

Expression of vonWillebrand factor protein (vWF) (DAKO) was detected with a goat anti-rabbit IgG-FITC secondary antibody (Sigma). Cells were fixed and incubated at room temperature for one hour with vWF, washed, and incubated for 30 minutes in the secondary antibody. After a final wash, cells were observed by fluorescence microscopy (UV, FITC filter). HUVECS again served as a positive control.

Matrigel Plugs

In one experiment SCID mice (Balb/Scid, Harlan Sprague Dawley) were injected subcutaneously with 0.5 ml Matrigel (Becton Dickinson) containing $5 \times 10^5 - 1 \times 10^6$ RESDECs. A second experiment was performed implanting a sponge containing the RESDECs into the solidified Matrigel. The Matrigel plugs were removed after 14, 21, 35, and 42 days. Vessels were observed by injecting high molecular weight FITC-dextran (Sigma) intravenously a few minutes before removing and fixing the plugs. Standard H/E slides were also prepared.

In Vivo Studies

Adherent RESDECs were harvested by trypsinization and mixed with the mouse mammary carcinoma, C755 cell line. In two separate experiments Balb/c-SCID mice were injected subcutaneously with either $1 \times 10^6$ C755 tumor cells, or $1 \times 10^6$ RESDECs, or with a mixture of $1 \times 10^6$ tumor cells and $1 \times 10^6$ RESDECs. After initial growth, tumors were measured by caliper every 3–5 days. Approximately three weeks after transplantation all mice were sacrificed for histochemical analysis of the grown tumors. Mice injected with only RESDECs failed to grow tumors.

Immunohistochemical Staining of Tumors

In the first experiment tumors were isolated and fixed in 10% formalin for the preparation of paraffin sections. To prepare frozen sections tumors were fixed in 2% paraformaldehyde. All sections were mounted onto Fisher Superfrost slides. Using the standard ABC technique (VectaStain Elite ABC kit, Vector labs) sections were processed for expression of HLA-class I A, B, C (W6/32 antibody, $IgG_{2a}$) and CD31 ($IgG_1$) (Novacastra, Vector). Mouse IgG1 (Sigma) and $IgG_{2a}$ (Southern Biotechnology) were used as isotype controls. The peroxidase activity was visualized with a DAB substrate (Vector) and sections were counterstained with hematoxylin.

Results

Derivation of Endothelial Cells from Rhesus Monkey ES Cells:

Rhesus monkey ES cells were grown in EGM2 medium containing VEGF, bFGF, EGF, and IGF as described in materials and methods. After approximately 5–10 days, these ES cells assumed a uniform morphology similar to elongated or stellate—shaped endothelial cells. In contrast, ES cells grown in medium supplemented with FBS alone differentiated into a heterogeneous cell population with no distinct endothelial-appearing cells. The potential endothelial cells were serially passaged and expanded for approximately 20 population doublings while grown in EGM2 with maintenance of a homogeneous appearance. As an initial test of endothelial cell characteristics, these cells were placed in Matrigel-based medium where they rapidly formed tube-like capillary structures similar those formed by HUVEC or other endothelial cell populations when placed in Matrigel-based medium. Cytogenetic studies showed all cells have a normal rhesus monkey 40 XY karyotype. These cytogenetic results were important to demonstrate that these cells were not transformed after prolonged culture, nor were they derived from potentially contaminating mouse embryonic fibroblast cells that are used for the growth of undifferentiated ES cells.

Electron micrographs of the rhesus ES cell-derived cells demonstrate typical endothelial cell features. These include multiple dense round or rod-shaped Weibel-Palade bodies, tight junctions between cells, and endocytic/exocytic vesicles.

Immunophenotyping

Next, immunohistochemical staining of these rhesus-derived endothelial-like cells demonstrated the presence von Willebrand factor (vWF), the ability for these cells to rapidly take-up acetylated LDL and the ability to bind the UEA-1 lectin. Flow cytometric studies confirmed high levels of UEA-1 binding, as well as expression of the integrin αvβ3 and the surface antigen CD146 recognized by the P1H12 antibody. These proteins have been shown to be important in endothelial cell-cell interactions. These results led us to call these rhesus embryonic stem cell-derived endothelial cells (RESDECs). Surprisingly, antibodies against the VEGF receptors flk-1 and flt-1 did not bind these RESDECs, though binding to HUVEC cells was also weak. However, an assay using biotinylated VEGF and secondary streptavidin-FITC showed binding to the RESDEC (and HUVEC) cells. Specificity of this binding was demonstrated by blocking with an anti-VEGF antibody. This results suggests that either the anti-human flk-1 and flt-1 antibodies did not cross-react with the rhesus-derived cells, or these cells express a different VEGF receptor. RT-PCR studies showed expression of flk-1 mRNA in the RESDECs, suggesting that the antibodies may not cross-react. Of course, it is possible that protein derived from this mRNA is not properly expressed on the cell surface.

The RESDEC cells do differ from HUVEC cells by lack of expression of CD31 and VE-cadherin, two surface antigens commonly, but not uniformly, found on the surface of endothelial cells. RT-PCR studies confirm absence of mRNA expression of these genes. However, some studies of mouse ES cell-derived endothelial cells also shows lack of CD31 and VE-cadherin in certain endothelial cell populations. While CD31 and VE-cadherin can serve as positive markers of endothelial cells, lack of expression does not preclude these being endothelial cells.

Angiogenesis from RESDEC Cells:

In vivo function of the RESDECs was first assessed by a Matrigel plug assay. Here, RESDECs were imbedded in a sponge that was suspended into solidified Matrigel. This Matrigel plug is then implanted subcutaneously in a severe combined immunodeficient (SCID) mouse. After approximately 28 days, the mouse was injeceted intravenously with a FITC-dextran solution, followed by plug removal and imaging. This demonstrated intense vascular localization toward the RESDEC containing sponge, a chemotactic-like event typical of endothelial cells. From the appearance of this vascularization, it is likely that this represents an area of murine vessel angiogenesis in response to RESDEC-derived factors. Indeed, subsequent analysis of RESDEC supernatant by ELISA demonstrated a significant level of vascular endothelial growth factor (VEGF) produced by these cells. However, basic fibroblast growth factor (bFGF), another angiogenic protein often produced by endothelial cells, was not measured in RESDEC culture supernatant.

To demonstrate neo-vessels produced by the RESDECs, $0.5-1.0 \times 10^6$ cells were evenly suspended in a Matrigel plug implanted subcutaneously in a SCID mouse. Again, the animals were injected with FITC-dextran, followed by plug removal and imaging. Here, larger vascular structures were seen and subsequent histological examination of the plug showed vascular formation by the RESDECs.

Next, to demonstrate the ability of RESDEC cells to contribute to active angiogenesis within tumors in vivo another SCID mouse model was used. Here, cells of the mouse mammary carcinoma line C755 were injected subcutaneously either alone or co-injected with an equivalent number of RESDECs. Tumor growth was measured at regular intervals and tumors grew significantly faster when co-injected with RESDECs. Importantly, $10^6$ RESDECs injected alone did not lead to any measurable tumor growth, demonstrating these cells are not directly tumorigenic. These tumors were highly vascular and immunohistochemical staining of the tumors with anti-human specific antibodies (that cross-react to rhesus monkey but not mouse cells) clearly demonstrate a contribution to the endothelium from the RESDEC cells. Staining of a substantial number of endothelial cells was positive using anti-MHC class I or anti-vWF antibodies in tumors co-injected with RESDEC cells, but endothelial cells in tumors derived from C755 alone were negative for these antigens.

We claim:

1. A method for directing the differentiation of primate embryonic stem cells into cells of the endothelial lineage comprising the steps of
    (a) culturing a culture of embryonic stem cells in a medium containing vascular endothelial cell growth factor, basic fibroblast growth factor, insulin-like growth factor and epidermal growth factor; and
    (b) sub-culturing the cells which have the morphology of endothelial cells to obtain a culture composed of cells over 90% of which are of endothelial lineage as determined by morphology.

2. A method as claimed in claim 1 wherein the primate cells are rhesus monkey cells.

3. A method as claimed in claim 1 wherein the primate cells are human cells.

4. A method as claimed in claim 1 wherein the medium for the culture of embryonic stem cells into endothelial cells also includes mammalian serum.

* * * * *

UNITED STATES PATENT AND TRADEMARK OFFICE
CERTIFICATE OF CORRECTION

| | | |
|---|---|---|
| PATENT NO. | : 7,176,023 B2 | Page 1 of 1 |
| APPLICATION NO. | : 10/287334 | |
| DATED | : February 13, 2007 | |
| INVENTOR(S) | : Dan S. Kaufman, Rachel Lewis and Robert Auerbach | |

It is certified that error appears in the above-identified patent and that said Letters Patent is hereby corrected as shown below:

Col. 1, Line 11, Insert:
This invention was made with United States govermment support awarded by the following agency:

NIH   HL52148

The United States has certain rights in this invention.

Signed and Sealed this

Eighth Day of May, 2007

JON W. DUDAS
*Director of the United States Patent and Trademark Office*